United States Patent [19]
Ko'oka et al.

[11] Patent Number: 4,473,567
[45] Date of Patent: Sep. 25, 1984

[54] SUBSTITUTED-IMIDAZOLIDINYL-3-CHLORO-3-CEPHEM-4-CARBOXYLIC ACID

[75] Inventors: Yoshinobu Ko'oka; Mariko Munekage, both of Hyogo; Hitoshi Minato, Osaka, all of Japan

[73] Assignee: Shionogi & Co., Ltd., Osaka, Japan

[21] Appl. No.: 367,974

[22] Filed: Apr. 13, 1982

Related U.S. Application Data

[60] Division of Ser. No. 149,836, May 14, 1980, Pat. No. 4,339,575, which is a continuation of Ser. No. 12,551, Feb. 15, 1979, abandoned.

[30] Foreign Application Priority Data

Feb. 23, 1978 [JP] Japan .................. 53-20675

[51] Int. Cl.³ .................. C07D 501/58; A61K 31/545
[52] U.S. Cl. .................. 424/246; 544/20; 544/16; 544/22
[58] Field of Search .................. 544/26, 16, 27, 20, 544/28, 22; 424/246

[56] References Cited

U.S. PATENT DOCUMENTS

| | | | |
|---|---|---|---|
| 3,925,372 | 12/1975 | Chauvette | 544/22 |
| 4,042,585 | 8/1977 | Koppel | 544/16 |
| 4,064,137 | 12/1977 | Hirai et al. | 424/246 |
| 4,091,213 | 5/1978 | Kaplan et al. | 424/246 |
| 4,098,888 | 7/1978 | Ochiai et al. | 424/246 |
| 4,125,716 | 11/1978 | Crast et al. | 426/246 |
| 4,217,275 | 8/1980 | Lim et al. | 544/20 |
| 4,252,950 | 2/1981 | Chauvette | 544/22 |
| 4,339,575 | 7/1982 | Ko'oka et al. | 544/20 |

*Primary Examiner*—Nicholas S. Rizzo
*Attorney, Agent, or Firm*—Wenderoth, Lind & Ponack

[57] ABSTRACT

7β-[2-(substituted or unsubstituted)-5-oxo-4-phenylimidazolidin-1-yl]-3-chloro-3-cephem-4-carboxylic acid represented by the formula:

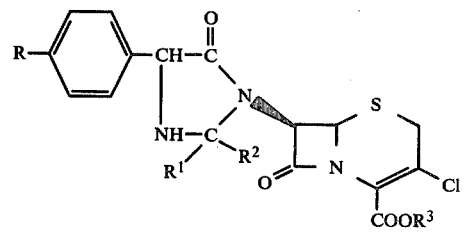

(wherein
R is hydrogen or hydroxy;
$R^1$ and $R^2$ each is hydrogen, alkyl, aralkyl or aryl, or when taken together, they represent alkylene optionally having a hetero atom in its skeleton; and
$R^3$ is hydrogen or an organic or inorganic base group to form a carboxylate salt group.)

11 Claims, No Drawings

SUBSTITUTED-IMIDAZOLIDINYL-3-CHLORO-3-CEPHEM-4-CARBOXYLIC ACID

This is a division of application Ser. No. 149,836, filed May 14, 1980, now U.S. Pat. No. 4,339,575, which is a continuation of application Ser. No. 12,551, filed Feb. 15, 1979, now abandoned.

I. COMPOUNDS

This invention relates to 7β-substituted-imidazolidinyl-3-chloro-3-cephem-4-carboxylic acids of the following formula:

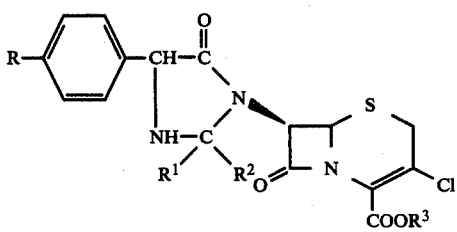

(wherein
R is hydrogen or hydroxy;
$R^1$ and $R^2$ each is hydrogen, alkyl, aralkyl or aryl, or when taken together, they represent alkylene optionally having a hetero atom in its skeleton; and
$R^3$ is hydrogen or an organic or inorganic base group to form a carboxylate salt group.).

Each of the symbols in the above formula and their definition are explained below:

Alkyl for $R^1$ and $R^2$ can be $C_1$ to $C_{18}$ straight, branched, cyclic or partly cyclic alkyl e.g. methyl, ethyl, propyl, isopropyl, butyl, isobutyl, secondary butyl, pentyl, isopentyl, neopentyl, t-pentyl, hexyl, octyl, cyclohexylethyl, nonyl, decyl, adamantyl, dodecyl, hexadecyl, or the like alkyls. Preferable alkyls are lower alkyl such as methyl, ethyl, and propyl.

Aralkyl for $R^1$ and $R^2$ can be $C_7$ to $C_{10}$ aralkyl optionally substituted e.g. by halogen, amino, $C_1$ to $C_3$ alkyl, $C_1$ to $C_3$ alkoxy, $C_2$ to $C_5$ alkanoylamino, or $C_2$ to $C_5$ alkanoyloxy. It can be benzyl, halobenzyl, methoxybenzyl, aminobenzyl, alkanoylaminobenzyl, phenethyl, phenylpropyl, thienylmethyl, or the like aralkyls. Preferable aralkyls for $R^1$ and $R^2$ are benzyl, chlorobenzyl, methoxybenzyl, and phenethyl.

Aryl for $R^1$ and $R^2$ can be monocyclic or dicyclic carbocyclic or heterocyclic aromatic group optionally substituted e.g. by halogen, nitro, amino, $C_1$ to $C_3$ alkyl, $C_1$ to $C_3$ alkoxy, $C_2$ to $C_5$ alkanoylamino, or $C_2$ to $C_5$ alkanoyloxy. It can be phenyl, tolyl, xylyl, mesityl, chlorophenyl, aminophenyl, methoxyphenyl, propoxyphenyl, acetaminophenyl, naphthyl, thienyl, pyridyl, or the like aryls. Preferable aryls for $R^1$ and $R^2$ are phenyl, tolyl, chlorophenyl, methoxyphenyl, and thienyl.

Alkylene optionally containing a hetero atom in its skeleton for $R^1$ and $R^2$ taken together can be $C_4$ to $C_{10}$ alkylene optionally having oxygen, sulfur, or nitrogen atom in place of methylene in the carbon chain. It can be tetramethylene, pentamethylene, hexamethylene, heptamethylene, azapentamethylene (e.g. ethyleneaminoethylene), oxaazapentamethylene or the like alkylenes. Preferable divalent groups for $R^1$ and $R^2$ are tetramethylene, pentamethylene, and hexamethylene.

The 4-carboxylate salt group for $R^3$ can be a pharmaceutically acceptable inorganic or organic base salt group conventional in the field of penicillin and cephalosporin drugs. It includes an alkali metal salt e.g. sodium or potassium salt, an alkaline earth metal salt e.g. calcium or magnesium salt, aluminum salt, ammonium salt; or organic base salt e.g. procain, dibenzylamine, N,N'-dibenzylethylenediamine, N-ethylpiperidine, or the like salts. Preferable carboxylate salts for $R^3$ are sodium, potassium and calcium salts.

Unless $R^1$ and $R^2$ are the same or symmetrical, the 2 position of the imidazolidine ring is asymmetric, and it is difficult to crystalize the compound. Therefore, $R^1$ and $R^2$ are preferably the same or symmetric. Especially when $R^1$ or $R^2$ is aryl, the product tends to be in Schiff base form, and less amount of the imidazolidinyl compound can be isolated in a pure form. Thus, a structure unconjugated to the 2 position of the imidazolidine ring is preferable. Larger $R^1$ or $R^2$ groups makes the compound lyophilic and thus preferable for pharmaceutical preparations requiring such character.

Lower alkyl or alkoxy has 1 to 4 carbon atoms.

Representative of the compounds [I] are the following:

7β-(2-ethyl-5-oxo-4-phenylimidazolidin-1-yl)-3-chloro-3-cephem-4-carboxylic acid;
7β-(2,2-dimethyl-5-oxo-4-phenylimidazolidin-1-yl)-3-chloro-3-cephem-4-carboxylic acid;
7β-(2-ethyl-2-methyl-5-oxo-4-phenylimidazolidin-1-yl)-3-chloro-3-cephem-4-carboxylic acid;
7β-(2-isobutyl-2-methyl-5-oxo-4-phenylimidazolidin-1-yl)-3-chloro-3-cephem-4-carboxylic acid;
7β-(2,2-tetramethylene-5-oxo-4-phenylimidazolidin-1-yl)-3-chloro-3-cephem-4-carboxylic acid;
7β-(2,2-pentamethylene-5-oxo-4-phenylimidazolidin-1-yl)-3-chloro-3-cephem-4-carboxylic acid;
7β-(2,2-ethyleneaminoethylene-5-oxo-4-phenylimidazolidin-1-yl)-3-chloro-3-cephem-4-carboxylic acid;
7β-(2-phenethyl-5-oxo-4-phenylimidazolidin-1-yl)-3-chloro-3-cephem-4-carboxylic acid;
7β-(2-phenyl-5-oxo-4-phenylimidazolidin-1-yl)-3-chloro-3-cephem-4-carboxylic acid;
7β-(2-methyl-2-phenyl-5-oxo-4-phenylimidazolidin-1-yl)-3-chloro-3-cephem-4-carboxylic acid;
7β-(2-ethyl-2phenyl-5-oxo-4-phenylimidazolidin-1-yl)-3-chloro-3-cephem-4-carboxylic acid;
7β-(2-p-methoxyphenyl-5-oxo-4-phenylimidazolidin-1-yl)-3-chloro-3-cephem-4-carboxylic acid;
7β-(2-methyl-2-p-chlorophenyl-5-oxo-4-phenylimidazolidin-1-yl)-3-chloro-3-cephem-4-carboxylic acid;
7β-(2-thienyl-2-methyl-5-oxo-4-phenylimidazolidin-1-yl)-3-chloro-3-cephem-4-carboxylic acid;
7β-(2,2-dimethyl-5-oxo-4-p-hydroxyphenylimidazolidin-1-yl)-3-chloro-3-cephem-4-carboxylic acid; and their salts.

II. PRIOR ART

Following prior art describes compounds somewhat related to the compounds of this invention:

Japanese Unexamined Patent Publication No. 52-100492

6β-(2-alkyl, alkenyl or phenyl-4-p-hydroxyphenyl-5-oxo-1-imidazolidinyl)penicillanic acid;

Japanese Examined Patent Publication No. 43-17194

7β-(2,2-dimethyl-4-phenyl-5-oxo-1-imidazolidinyl)-cephalosporanic acid;

Japanese Examined Patent Publication No. 47-42795

7β-(2,2-dimethyl-4-phenyl-5-oxo-1-imidazolidinyl)-3-methyl-3-cephem-4-carboxylic acid;

Japanese Unexamined Patent Publication No. 48-64094

7β-(2,2-hydrogen, alkyl or aryl-4-thienyl or phenyl-5-oxo-1-imidazolidinyl)-3-methyl-3-cephem-4-carboxylic acid;

Japanese Examined Patent Publication No. 46-4825

7β-(2,2-dimethyl-3-nitroso or hydrogen-5-oxo-1-imidazolidinyl)-3-methyl-3-cephem-4-carboxylic acid; and Japanese Examined Patent Publication No. 48-40794

7β-(2,2-dimethyl-3-nitroso-4-phenyl-5-oxo-1-imidazolidinyl)-3-bromomethyl-3-cephem-4-carboxylic acid 1-oxide and ester derivatives thereof.

The inventors of the subject matter disclosed in these patent applications claim stabilization of their compounds especially in an aqueous solution as compared with their parent arylglycylamino compounds, non-toxicity, good absorption by oral administration, and good pharmacological character in the human body. They are also said to be useful as intermediates.

III. STARTING MATERIAL

The starting material of the formula:

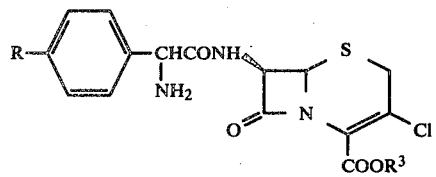

[II]

(wherein R and $R^3$ each is the same as mentioned above) has been prepared according to the method as described in Japanese Patent Unexamined Publication No. 49-110,689. For example, 7-phenoxyacetamidocephalosporanic acid is treated with thiourea to give an isothiuronium salt and reduced with zinc and excess amount of 90% formic acid to yield 7-phenoxyacetamido-3-exomethylenecephem-4-carboxylic acid. The product is esterified with p-nitrobenzyl bromide in the presence of a hydrogen halide acceptor and subjected to ozonolysis in methylene chloride at −70° C., followed by reductive fission with sulfur dioxide giving 7-phenoxyacetamido-3-hydroxy-3-cephem-4-carboxylic acid p-nitrobenzyl ester. This is treated with phosphorus trichloride in N,N-dimethylformamide to chlorinate the 3 position, and then treated with phosphorus pentachloride by the action of pyridine, methanol, and water successively to give 7-amino-3-chloro-3-cephem-4-carboxylic acid p-nitrobenzyl ester. The latter compound is acylated with p-phenylglycyl chloride hydrochloride or D-p-hydroxyphenylglycyl chloride hydrochloride to give cefaclor p-nitrobenzyl ester which gives the objective compound [II] on fission of the p-nitrobenzyl ester group.

The starting material [II] (R=H) which exhibits excellent antibacterial activity in itself, is a well-known compound and is generically called cefaclor.

IV. SYNTHESIS

1. Cyclization

Compounds [I] may be prepared by reacting 7β-(α-D-phenylglycyl)amino-3-chloro-3-cephem-4-carboxylic acid or the salts thereof [II] with an aldehyde or ketone [III].

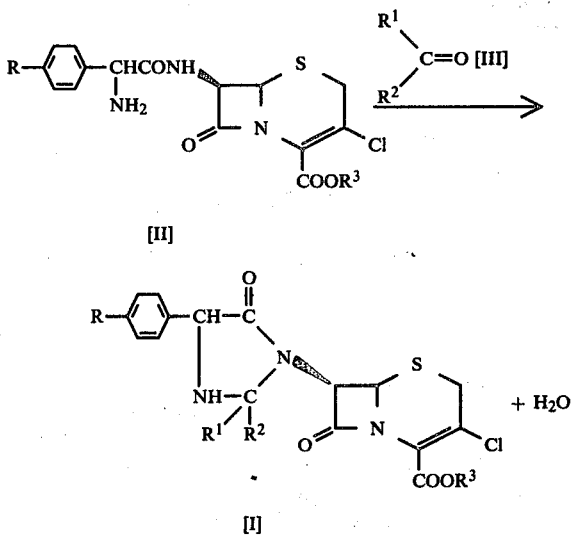

(wherein R, $R^1$, $R^2$, and $R^3$ each has the same meaning as mentioned above.)

The amount of aldehydes or ketones [III] is preferably 1 mole or more per mole of the starting material [II].

Preferably, this reaction may be carried out in a solvent. Any solvent, which does not disturb the reaction, may be employed. Preferable solvents are alcohols, amides, sulfoxides, water, and the like high-polar industrial solvents. When water is employed as a solvent, it is preferred to make the reaction medium neutral or slightly basic. It is possible to use a large excess amount of aldehyde or ketone, thus serving as both the reagent and solvent.

This reaction proceeds enough at room temperature or under cooling, although it is accelerated by warming. Starting material [II] is difficultly soluble in an aprotic organic solvent or aqueous neutral medium, but it dissolves as the reaction proceeds until the end of the reaction. The reaction is finished when the starting material dissolves completely.

This reaction may be accelerated by removing water produced during the reaction, for example, by azeotropic distillation, addition of calcium carbonate, magnesium carbonate, molecular sieves, or sodium carbonate, and the like method.

In aqueous acetone, the reaction is an equilibrium reaction, with a neutral or basic medium favoring formation of the objective product [I].

Thus, prepared compounds [I] may be isolated by the addition of insoluble solvents (e.g. methanol, ethanol, water, petroleum ether-hexane, benzene), extraction with organic solvent, recrystallization, and other conventional methods. These methods may be employed alone or in combination.

2. Deprotection at 4-carboxylic group

Compounds [I] in which the carboxy group on the cephem ring is optionally protected are deprotected in a conventional manner to yield the objective compound.

Carboxy protecting groups mean protecting groups conventional in penicillin or cephalosporin chemistry, for example, ester forming groups such as acyloxymethyl, acyloxyethyl, phthalidyl, indanyl, benzyl, anisyl, nitrobenzyl, trichloroethyl or phenacyl or the like carboxy protecting groups described in Japanese Unexamined Patent Publication No. 49-110689.

Deprotection may conventionally be carried out under conditions which do not cause cleavage of the imidazolidine ring. The conditions are set up according to the type of protecting groups.

3. Imidazolidine ring rupture vs. closure

Compounds [I] and [IV] are in equilibrium. As a result, Compound [IV] can be cyclized to yield objective Compound [I] by adjusting pH, polarity, reaction temperature or the like factors of reaction conditions.

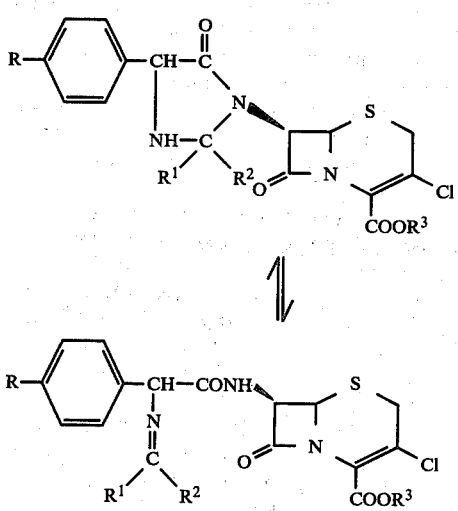

V. CHARACTERISTICS

Compounds [I] are more easily handled than the compound [II], because crystals of the former are:
(1) large,
(2) readily purified, and
(3) very stable.

Characteristics of the stability are shown in Table 1.

TABLE 1

| Data on Stability of Compound I ($R^1 = R^2$ = Me) | | | |
|---|---|---|---|
| | Heat (105° C., 3 hr) | Light fade test 50,000 Lux 10 hr. | Humidity 37% Relative humidity 90%, 2 weeks. |
| Compound [I] | pale redish | colorless | slightly pale yellowish |
| Starting Compound [II] | pale yellow | pale yellowish | pale yellow |

Compounds [I] may be used to reproduce the starting compound [II] by hydrolysis.

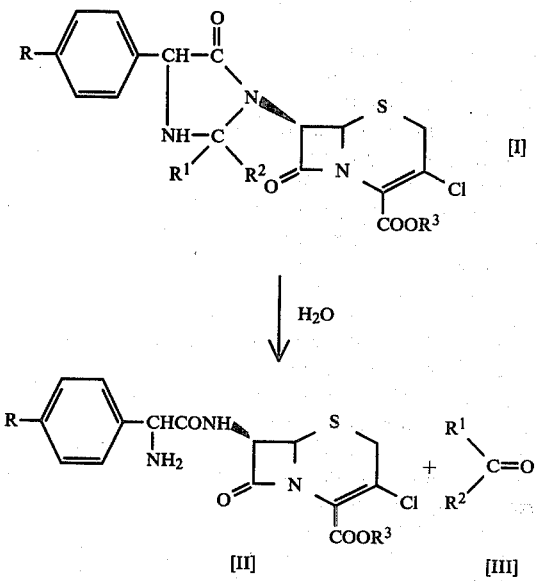

(wherein R, $R^1$, $R^2$, and $R^3$ each has the same meaning as mentioned above.)

This reaction may be also carried out in a polar-solvent such as alcohols, dioxane, tetrahydrofuran, amides or sulfoxides, haloalkanes, esters or the like solvents.

This reaction may be carried out at 0° C. to 100° C., preferably at about room temperature. The reaction ordinarily is complete within 2 hours. When the reaction temperature is low or the starting material is not so reactive, it takes a longer time. The reaction is accelerated on addition of acids such as mineral acids, carboxylic acids, sulfonic acids, or the like.

Compounds [II] may be readily obtained in a form of crystals by adjusting the pH to about 4 to 5 with acid or base regulated to a suitable concentration, followed by filtration and drying in a conventional manner. Compounds [II] may form the corresponding salts.

Thus prepared 7β-(α-D-phenylglycyl)amino-3-chloro-3-cephem-4-carboxylic acid is in a form of large prisms showing mp. 199° C. and is relatively stable. This reaction may be employed as a novel process for preparation of Compounds [I].

Thus, a difficult point in preparation of the rather unstable starting cephalosporin has been resolved by the above process (II→I→II).

IV. HOW TO USE

Compounds [I] are novel substances showing potent antibacterial activity and are useful as medicines, veterinary drugs, and disinfectants. For example, they are conventionally given orally or parenterally to humans or animals at a daily dose of e.g. 0.05 to 200 mg/kg body weight.

They are valuable antibiotics as active as the starting compounds [II] against various gram-positive and negative bacteria, and are useful as drugs for human and veterinary uses. They can be used for treating or preventing infections caused by gram-positive bacteria (e.g. *Staphylococcus aureus, Streprococcus pyogenes, Bacillus subtilis, bacillus cereus, Streptococcus pneumoniae*) or gram-negative bacteria (e.g. *Escherichia coli, Klebsiella pneumoniae, Proteus mirabilis, Proteus vulgaris, Haemophilis influenza*). The compounds can be used also as disinfectants for preventing decay of perishables, additives to foodstuffs, or preventing bacterial growth in hygenic materials.

Further, Compounds [I] are also useful intermediates for preparing useful antibiotics within or beyond the scope of Componds [I].

The Compounds [I] can be used in a wide variety of oral or parenteral dosage forms solely or in admixture with other coacting substances. The pharmaceutical compositions may be a mixture of 0.01 to 99% of Compound [I] with a pharmaceutical carrier which can be a solid material or liquid material in which the compounds are dissolved, dispersed, or suspended. They can be in a unit dosage form. The solid compositions can take the form of tablets, powder, dry syrups, troches, granules, capsules, pills, suppositories, or like solid preparations. The liquid compositions can take the forms of injection, ointments, dispersions, inhalant, suspension, solutions, emulsions, syrups, or elixirs. They may be flavored, colored, and tablets, granules, and capsules may be coated.

All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders; (e.g. starch, acacia, gelatin, glucose, sodium alginate, tragacanth, carboxymethylcellulose, syrup, sorbitol, polyvinylpyrrolidone); disintegrators (e.g. starch, agar, carbonates, sodium laurylsulfate); lubricant (e.g. stearic acid, talc, paraffin, boric acid, silica, sodium benzoate, polyethylene glycol, cacao oil, magnesium stearate), emulsifying agents (e.g. lecithin, sorbitan monooleate, acacia); suspending agents (e.g. sorbitol, methyl cellulose, glucose, or sugar syrup, gelatin, hydroxyethylcellulose, carboxymethylcellulose, aluminium stearate gel, hydrogenated fats); solvents (e.g. water, buffer, peanut oil, sesame oil, methyl oleate); preservatives (e.g. methyl or ethyl p-hydroxybenzoate, sorbic acid); edible coloring agents, aromatic substances, solubilizing agents, buffers, stabilizing agents, analgesics, dispersing agents, wetting agents, antioxidants, and the like can be used if the agents do not exert adverse effect on the compounds, according to the methods conventional in the art.

Compounds [I] having a carboxylic acid salt group are soluble in water, and conveniently used as solutions for intravenous, intramuscular, or subcutaneous injection according to a conventional method. The compounds can be dissolved in aqueous or oily solvents for injection to give a solution in an ampoule, but generally, more prolonged storage is possible by making a vial preparation containing crystals, powder, microcrystals, or lyophilizate of Compound [I], and dissolving or suspending the drug before use with the said solvents for injection. The preparation may contain preferably said preservative. The vial preparation or injection can be given to a patient at a daily dose of e.g. 5 to 50 mg/kg body weight depending on the infectious bacteria, condition of the patient, and interval of the administration.

Further, Compounds [I] can be used as suppositories, ointments for topical or ocular use, powders for topical use, and like preparations preparable according to methods well known to those skilled in the art. Representative suppository bases are cacao butter, glycerogelatin, macrogel and the like, and representative ointment bases are vaselin, paraffin, liquid paraffin, purified lanolin, glycols and the like. The preparation can contain 0.01 to 99% of the Compound [I] together with a necessary amount of pharmaceutical carrier given above and if required, together with a small amount of surface active agent. A necessary amount e.g. 1 µg to 100 mg of the preparation can be applied.

Compounds [I] can be absorbed through the digestive organ and can be administered to human or veterinary subject as powder, tablets, granules, capsules, dry syrup, emulsions, solution, suspension, and like oral preparations. These may be pure compounds or a composition comprising Compounds [I] and said pharmaceutical carrier. The preparation can be made according to the methods conventional in the art, and can be administered to a patient at a daily dose of e.g. 10 to 50 mg/kg body weight depending on the condition of patient and the disease.

This invention also provides a method for treating or preventing human or veterinary bacterial infections by administering to the human or animal subject an effective amount of Compound [I] at a daily dose of e.g. 5 to 50 mg/kg body weight for injection or e.g. 5 to 200 mg/kg body weight for oral administration, or 10 µg to 1 mg for topical application, at intervals of e.g. 3 to 12 hours.

The method is applicable for treating or preventing some diseases by bacteria sensitive to Compounds [I] e.g. pneumonia, bronchitis, pneumonitis, respiratory tract infections, empyema, nasopharyngitis, tonsillitis, rhinitis, dermatitis, pustulosis, ulceration, abses, wound and soft tissue infections, ear infections, osteomylitis, septicemia, gastroenteritis, enteritis, urinary tract infections, and pyelonephritis when caused by bacteria sensitive to Compound [I].

Preferably Compounds [I] are given to a patient in a form of pharmaceutical preparations e.g. powder, dry syrup, tablets, troches, granules, capsules, pills, suppositories, injection, ointments, dispersions, inhalant, suspensions, solutions, emulsions, syrups, and elixirs. They may be in a unit dosage form e.g. tablets, troches, capsules, injections, vials, granules, or powder in a separate container or package.

Most preferable Compound [I] for the methods and pharmaceutical preparations are following compounds:

7β-(2-ehtyl-5-oxo-4-phenylimidazolidin-1-yl)-3-chloro-3-cephem-4-carboxylic acid;

7β-(2-ethyl-5-oxo-4-phenylimidazolidin-1-yl)-3chloro-3-cephem-4-carboxylic acid pharmaceutical acceptable salt;

7β-(2,2-dimethyl-5-oxo-4-phenylimidazolidin-1-yl)-3-chloro-3-cephem-4-carboxylic acid;

7β-(2,2-dimethyl-5-oxo-4-phenylimidazolidin-1-yl)-3-chloro-3-cephem-4-carboxylic acid pharmaceutical acceptable salt;

7β-(2-ethyl-2-methyl-5-oxo-4-phenylimidazolidin-1-yl)-3-chloro-3-cephem-4-carboxylic acid;

7β-(2-ethyl-2-methyl-5-oxo-4-phenylimidazolidin-1-yl)-3-chloro-3-cephem-4-carboxylic acid pharmaceutical acceptable salt;

7β-(2-isobutyl-2-methyl-5-oxo-4-phenylimidazolidin-1-yl)-3-chloro-3-cephem-4-carboxylic acid;

7β-(2-isobutyl-2-methyl-5-oxo-4-phenylimidazolidin-1-yl)-3-chloro-3-cephem-4-carboxylic acid pharmaceutical acceptable salt;

7β-(2,2-tetramethylene-5-oxo-4-phenylimidazolidin-1-yl)-3-chloro-3-cephem-4-carboxylic acid;

7β-(2,2-tetramethylene-5-oxo-4-phenylimidazolidin-1-yl)-3-chloro-3-cephem-4-carboxylic acid pharmaceutical acceptable salt;

7β-(2,2-pentamethylene-5-oxo-4-phenylimidazolidin-1-yl)-3-chloro-3-cephem-3-carboxylic acid;

7β-(2,2-pentamethylene-5-oxo-4-phenylimidazolidin-1-yl)-3-chloro-3-cephem-4-carboxylic acid pharmaceutical acceptable salt;

7β-(2,2-ethyleneaminoethylene-5-oxo-4-phenylimidazolidin-1-yl)-3-chloro-3-cephem-4-carboxylic acid;

7β-(2,2-ethyleneaminoethylene-5-oxo-4-phenylimidazolidin-1-yl)-3-chloro-3-cephem-4-carboxylic acid, pharmaceutical acceptable salt;

7β-(2-phenethyl-5oxo-4-phenylimidazolidin-1-yl)-3-chloro-3-cephem-4-carboxylic acid;

7β-(2-phenethyl-5-oxo-4-phenylimidazolidin-1-yl)-3-chloro-3-cephem-4-carboxylic acid pharmaceutical acceptable salt;

7β-(2,2-dimethyl-5-oxo-4-p-hydroxyphenylimidazolidin-1-yl)-3-chloro-3-cephem-4-carboxylic acid; and 7β(2,2-dimethyl-5-oxo-4-p-hydroxyphenylimidazolidin-1-yl)-3-chloro-3-cephem-4-carboxylic acid pharmaceutical acceptable salt.

Following examples are given to show the embodiment of this invention. The melting points are determined from the differential thermal analysis curves.

When $R^1$ and $R^2$ are different from each other, the product [I] is a mixture of stereoisomers at the 2-asymmetric carbon of the imidazolidine ring.

EXAMPLE 1

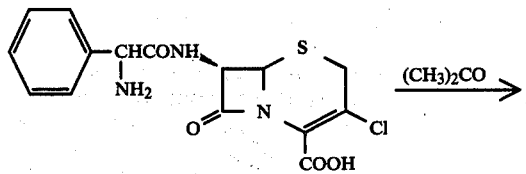

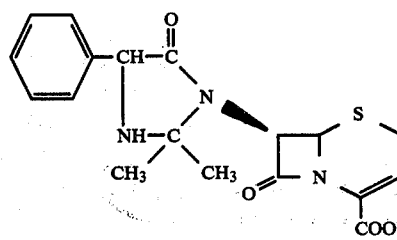

(1) A suspension of 4 g of 7β-(α-D-phenylglycyl)amino-3-chloro-3-cephem-4-carboxylic acid in 300 ml of acetone is refluxed for 2 hours, concentrated to 100 ml, refluxed under heating again for 1 hour, and then concentrated to remove acetone. The residue is mixed with 30 ml of methanol and stirred at room temperature. The separated solid is collected by filtration and dried under reduced pressure to yield 3.8 g of 7β-(2,2-dimethyl-5-oxo-4-phenylimidazolidin-1-yl)-3-chloro-3-cephem-4-carboxylic acid in 87.0% yield. m.p. 194° C. (decomposition).

$[\alpha]_D^{20}+190°$ C. (0.1N-HCl).

IR: $\nu_{max}^{KBr}$3400 broad, 1789, 1718, 1600, 1417, 1365, 1258, 1170, 1124, cm$^{-1}$.

NMR: $\delta_{ppm}^{CD3SOCD3}$ 1.37s3H, 1.43s3H, (3.64+3.88)ABq(18 Hz)2H, 4.70s1H, (5.07+5.40)ABq(4 Hz), 7.60-7.25 broad, 7.95 m.

(2) To a solution of 0.15 g of 7β-(α-D-phenylglycyl)amino-3-chloro-3-cephem-4-carboxylic acid in 30 ml of water are added 30 ml of 0.1N acetate buffer and 30 ml of acetone, and the mixture is allowed to stand at room temperature for 2 hours. A thin-layer chromatogram on cellulose powder using tetrahydrofuran-water (1:5) as developing solvent shows the spots of about equal amounts of 7β-(2,2-dimethyl-5-oxo-4-phenylimidazolidin-1- yl)3-chloro-3-cephem-4-carboxylic acid and the starting material.

EXAMPLE 2

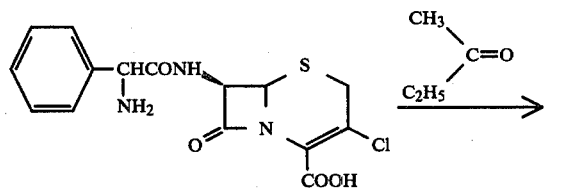

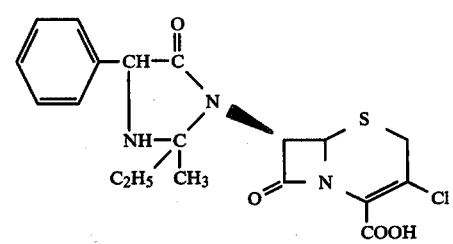

A suspension of 1.76 g of 7β-(α-D-phenylglycyl)amino-3-chloro-3-cephem-4-carboxylic acid in 200 ml of methyl ethyl ketone is refluxed under heating for 1 hour while removing the resulting water by means of Molecular Sieves 4A in Dean Stark water separator, and the resulting transparent solution is concentrated to about 5 ml, mixed with 10 ml of methanol and allowed to stand for 30 minutes. The separated precipitate is collected by filtration and dried under reduced pressure to yield 7β-(2-ethyl-2-methyl-5oxo-4-phenylimidazolidin-1-yl)-3-chloro-3-cephem-4-carboxylic acid.

mp. 188°–189.5° C. (decomposition)

IR: $\nu_{max}^{KBr}$ 1788, 1766(sh), 1710, 1595(br) cm$^{-1}$.

NMR: $\delta_{ppm}^{D20}$ 1.00t(7 Hz)3H, 1.60–2.05m2H, 3.57+3.93ABq(18 Hz) 2H, 4.85s, 5.28s2H, 7.57s5H (internal standard: DSS).

The product is allowed to stand to give 7β-[α-D-phenyl-α-(2-butylideneamino)acetamido]-3-chloro-3-cephem-4-carboxylic acid, since the following reaction proceeds.

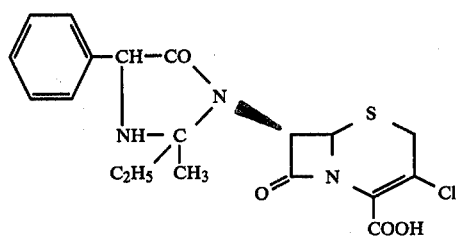

-continued

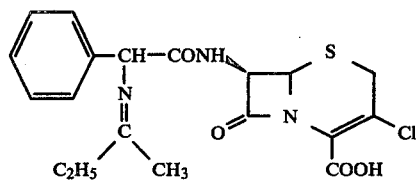

NMR: $\delta_{ppm}{}^{D_2O}$ 1.00t(7 Hz)3H, 2.21s3H, 2.58q(7 Hz)3H, 3.40+3.80 ABq(18 Hz), 4.74s, 5.13d(4.5 Hz), 5.70d(4.5 Hz), 7.53s5H (internal standard: DSS).

EXAMPLE 3

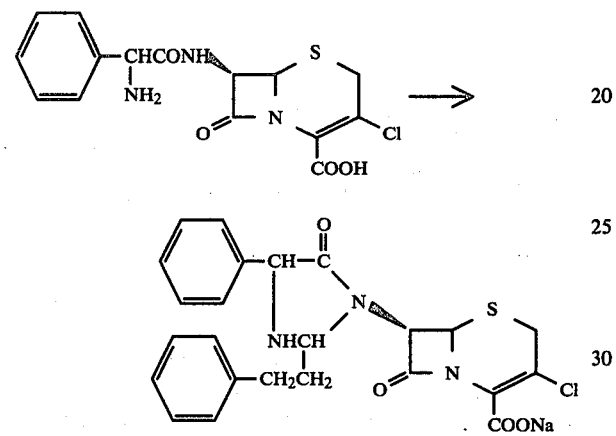

To 100 ml of an aqueous suspension of 6 g of 7β-(α-D-phenylglycyl)amino-3-chloro-3-cephem-4-carboxylic acid is added a mixture of 2.3 ml of 2-phenylpropionaldehyde and 2.5 ml of 20% aqueous hydroxide solution to yield sodium 7-(2-phenethyl-5oxo-4-phenyl-1-imidazolidinyl)-3-chloro-3-cephem-4-carboxylate, and the latter is mixed with 3N hydrochloric acid to yield the corresponding free acid.

EXAMPLE 4

Compounds shown in Table 2 may be prepared from 7β-(α-D-phenylglycyl)amino-3-chloro-3-cephem-4-carboxylic acid and the corresponding aldehyde or ketone in a manner similar to that described in Example 1, 2 or 3.

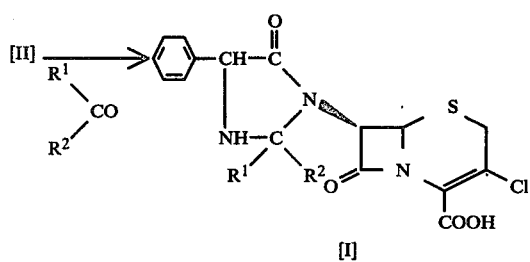

TABLE 2

| No. | R¹ | R² |
|---|---|---|
| 1 | —H | —C$_2$H$_5$ |
| 2 | —H | —C$_6$H$_5$ |
| 3 | —H | —C$_6$H$_4$OCH$_3$ |

TABLE 2-continued

| No. | R¹ | R² |
|---|---|---|
| 4 | —H | (thienyl) |
| 5 | —CH$_3$ | —CH$_2$CH(CH$_3$)$_2$ |
| 6 | —CH$_3$ | —C$_6$H$_5$ |
| 7 | —CH$_3$ | —C$_6$H$_4$Cl |
| 8 | —(CH$_2$)$_5$— | |
| 9 | —CH$_2$CH$_2$NHCH$_2$CH$_2$— | |

EXAMPLE 5

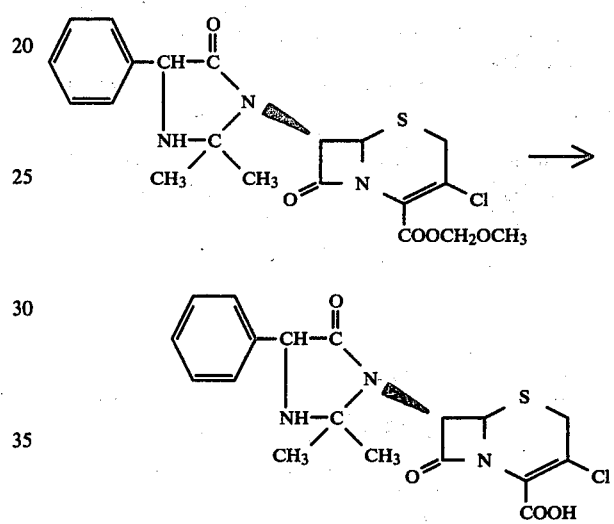

A solution of 0.5 g of methoxymethyl 7β-(2,2-dimethyl-5-oxo-4-phenylimidazolidin-1-yl)-3-chloro-3-cephem-4-carboxylate in 10 ml of methanol is refluxed for 1 hour, and the reaction mixture is concentrated to a third volume and stirred for 30 minutes under ice-cooling. The resulting precipitate is collected by filtration and dried under reduced pressure to yield 0.4 g of 7β-(2,2-dimethyl-5oxo-4-phenylimidazolidin-1-yl)-3-chloro-3-cephem-4-carboxylic acid.

The starting material may be prepared by esterifying 7β-(α-D-phenylglycyl)amino-3-chloro-3-cephem-4-carboxylic acid with methoxymethyl chloride, followed by treating with acetone.

EXAMPLE 6

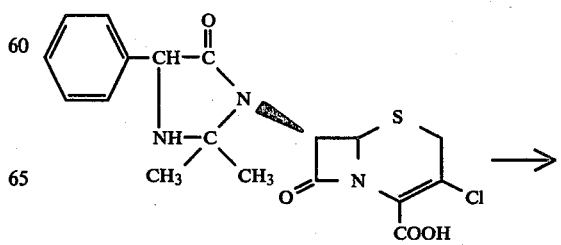

TABLE 3

As shown in Table 3, a reaction of the carbonyl compound with the starting material [II] produces compound (Ia) even when water is used as a solvent.

| Compound No. | Amount of Compound (II) mg (mmole) | H₂O (ml) | Reagent (mg) | Temp. | Time | R¹ | R² | Yield mg | Yield % |
|---|---|---|---|---|---|---|---|---|---|
| 1 | 184 (0.5) | 2 | NaHCO₃ (42) CH₃CHO (80) | rt | 5 hr | —CH₃ —H | —H —CH₃ | 142 | 72 |
| 2 | 184 (0.5) | 2 | NaHCO₃ (42) CH₃COCH₂CH₃ (0.75 ml) NaHCO₃ (42) | rt | 6.5 hr | —CH₃ —CH₂CH₃ | —CH₂CH₃ —CH₃ | 51.0 + 50.8 | 24.2 + 24.1 |
| 3 | 184 (0.5) | 3 | 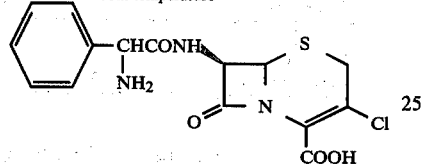 (286) | rt | 7.5 hr | —(CH₂)₄— | | 100 | 46.1 |

(Note)
hr = hour
rt = room temperature

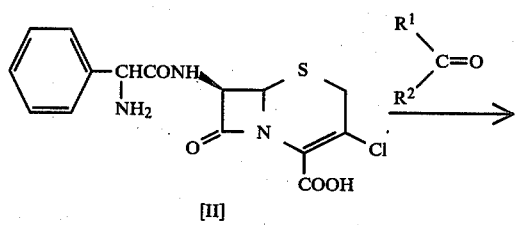

A solution of 3 g of 7β-(2,2-dimethyl-5-oxo-4-phenyl-1-imidazolidinyl)-3-chloro-3cephem-4-carboxylic acid in a mixture of 50 ml of methanol and 5 ml of 0.5N hydrochloric acid is adjusted to pH 4 to 5 with aqueous ammonia. The resulting precipitate is collected by filtration, washed with cold water, and dried at 25° C. under reduced pressure to yield 2.2 g of 7β-(α-D-phenylglycyl)amino-3-chloro-3-cephem-4-carboxylic acid as pure prisms in 81% yield.

m.p. 199° C. (decomposition).
$[\alpha]_D^{20}$ +116° (water).
UV: $E_1$ $_{cm}$¹% 249.
IR: $\nu_{max}^{KBr}$ 3340, 3030, 1790, 1710, 1620, 1520, 1370, 1270, 1253, 1190, 1145, 1112, 1025 cm⁻¹.
MNR: $\delta_{ppm}^{D2O+DCl}$ (3.82+3.48)ABq(J=18.6 Hz), (3.48+3.82)ABq (J=18.6 Hz), 4.88s, 5.15d(J=6 Hz), 5.27s, 5.75d (J=6 Hz),7.55s.

EXAMPLE 7

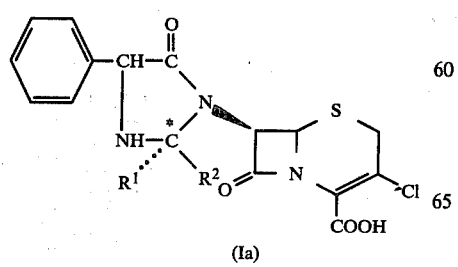

For example, Compound No. 2 gives Compound (Ia) in the following reaction:

(1) To a suspension of 184 mg (0.5 mmole) of 7β-(α-D-phenylglycyl)amino-3-chloro-3-cephem-4-carboxylic acid (II) in 2 ml of water is added 42 mg (0.5 mmole) of sodium hydrogencarbonate, and the mixture is stirred at room temperature for 30 minutes, mixed with 0.75 ml of methyl ethyl ketone, stirred again at room temperature for 6.5 hours, adjusted to pH 1.5 to 2.0 with 0.5 ml of 1N hydrochloric acid, and extracted with 5 ml of ethyl acetate. The aqueous layer is separated, saturated with sodium chloride and reextracted twice with ethyl acetate. The combined ethyl acetate layers are washed with saturated brine, dried, and evaporated to yield 167.6 mg of the residue as pale yellow powder.

(2) A part of the above residue (61.9 mg) is washed with methylene chloride to yield 51.0 mg of 7β-(2-ethyl-2-methyl-5-oxo-4-phenylimidazolidin-1-yl)-3-chloro-3-cephem-4-carboxylic acid (Ia) as pale yellow powder.

(3) A part of the residue (95.2 mg) is washed with methanol to yield 50.8 mg of 7β-(2-methyl-2-ethyl-5-oxo-4-phenylimidazolidin-1-yl)-3-chloro-3-cephem-4-carboxylic acid (Ia).

Physical constants of the products (Ia) prepared under condition described in Table 3 are shown in Table 5.

EXAMPLE 8

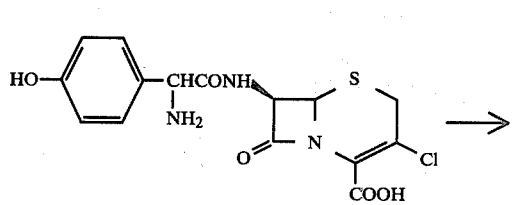

-continued

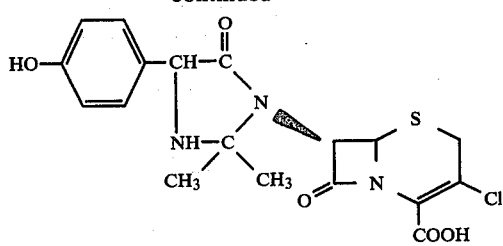

To a suspension of 190 mg of 7β-(α-D-p-hydroxyphenylglycyl)amino-3-chloro-3-cephem-4-carboxylic acid in 25 ml of acetone is added 10 mg of p-toluenesulfonic acid monohydrate, and the mixture is refluxed for 2 hours under heating. After cooling, the mixture is filtered and the filtrate is concentrated under reduced pressure. The residue is mixed with acetone and the insoluble materials are filtered off to yield 110 mg of 7β-(2,2-dimethyl-5-oxo-4-p-hydroxyphenylimidazolidin-1-yl)-3-chloro-3-cephem-4-carboxylic acid as amorphous powder.

IR: $\nu_{max}^{Nujol}$ 3200 broad, 1778, 1692, 1610, 1515, 1270, 2340, 1178 cm$^{-1}$.

NMR: $\delta^{DMSO-d6}$ 1.38s3H, 1.43s3H, (3.72+3.88)ABq(18 Hz)2H, 4.67s1H, (5.18+5.40)ABq(4 Hz)2H, 6.75-7.4m4H.

TLC: Rf 0.15 [precoated plate (SiO$_2$). EtOAc-:AcOH:H$_2$O=8:1:1].

Experiment 1 (Suppositories)

Cefaclor acetonide (test compound: 500 mg) or Cefaclor (reference compound: 500 mg) and Witepsol W-35 (synthetic glycerides distributed by Dynamit Novel Chemicals AG: 5 g) were mixed together until a uniform suspension resulted. Sixty milligrams of a suppository was administered rectally to a male rat weighing 200±30 gram. Three rats each at 15, 30, and 60 minutes after administration of each sample were sacrificed. Blood was collected from inferior vena cava. The blood was centrifuged to give plasma. The plasma was mixed with methanol and centrifuged to remove serum protein. When the sample was cefaclor, the obtained plasma was washed with chloroform to remove an oily physiological substance possessing similar behavior to cefaclor on chromatogram. The obtained plasma was subjected to high performance liquid chromatography. The peak of the sample was measured and the blood level was calculated in terms of microgram sample per milliliter blood of the rat. The data was summarized below in Table 4. Given values are the mean from three rats treated equally.

TABLE 4

| Compound | Blood level (μg/ml) at various times (min) after the application of the drug | | |
|---|---|---|---|
| | Time | | |
| | 15 | 30 | 60 |
| Cefaclor (Reference) | 0.8 | 1.5 | 1.4 |
| Cefaclor acetonide | 2.0 | 2.4 | 3.2 |

Experiment 2 (Capsules)

Two hundred grams of Compound [I]($R^1=R^2=CH_3$; $R^3$32 H) is intimately mixed with 50 g of corn starch, 5 g of talc and 1 g of magnesium stearate and pulverized. A thousand hard gelatin capsules are filled with the powder so made to give capsules each containing 200 mg of the active ingredient. One capsule each is given thrice a day to an adult patient suffering from respiratory tract infection.

TABLE 5

| Comp. No. | m. p. | IR: $\gamma_{max}^{KBr}$ (cm$^{-1}$) | NMR: (Hz value represent the coupling constant.) | |
|---|---|---|---|---|
| | | | $\delta_{ppm}^{D6-DMSO}$ (internal standard: TMS) | $\delta_{ppm}^{D2O}$ (internal standard: DSS) |
| 1 | 240° C. (decomposition) | 1765, 1727, 1585 (br, w). | isomer A<br>1.32d(6Hz)3H, 3.65 + 4.08ABq (18Hz), 4.65s, 4.83q(6Hz), 5.23d(5Hz), 5.44d(5Hz), 7.25-7.72m. | isomer A<br>1.46d(6Hz)3H, 3.58 + 3.95ABq (18Hz), 4.77s, 4.94q(6Hz), 5.30s2H, 7.58s5H. |
| | −165° C. (coloring) | | isomer B<br>1.40d(6Hz)3H, 3.67 + 3.85ABq (18Hz), 4.65s, 4.83q(6Hz), 5.20d(5Hz), 5.40d(5Hz), 7.25-7.72m5H. | isomer B<br>1.51d(6Hz)3H, 3.49 + 3.88ABq (18Hz), 4.77s, 4.94q(6Hz), 5.30s2H, 7.58s5H. |
| | Treatment with methylene chloride | | | |
| 2 | 290° C. (decomposition) | 1780, 1765sh, 1711, 1595 (br, w). | isomer A<br>0.93t(7Hz)3H, 1.37s3H, 1.46-1.88m2H, 3.66 + 3.91ABq (18Hz), 4.76s1H, 5.22d(4.5Hz), 5.32-5.51m, 7.25-7.70. | isomer A<br>1.00t(7Hz)3H, 1.53s3H, 1.87q(7Hz)2H, 3.58 + 3.95ABq (18Hz), 4.86s, 5.30s2H, 7.59s5H. |
| | −150° C. (coloring) | | isomer B<br>1.08t(7Hz)3H, 1.42s3H, 1.46-1.88m2H, 3.66 + 3.91ABq (18Hz), 4.76s1H, 5.22d (4.5Hz), 5.32-5.51m, 7.25-7.70. | isomer B<br>1.00t(7Hz)3H, 1.53s3H, 1.87q(7Hz)2H, 3.58 + 3.95ABq (18Hz), 4.86s, 5.30s2H, 7.59s5H. |
| | Treatment with methanol | | | |
| | 188-189.5° C. (decomposition) | 1788, 1766sh, 1710, 1595br. | | isomer A<br>1.00t(7Hz)3H, 1.60-2.05m 2H, 3.57 + 3.93ABq(18Hz)2H, 4.85s, 5.28s2H, 7.57s5H. |
| | | | | isomer B<br>1.00t(7Hz)3H, 1.60-2.05m 2H, 3.57 + 3.93ABq(18Hz)2H, 4.85s, 5.28s2H, 7.57s5H. |
| 3 | 180-198° C. | 1780, 1690br, 1610 (br, w). | 1.45-2.15m8H, 3.64 + 3.87ABq | |

TABLE 5-continued

| Comp. No. | m. p. | IR: $\gamma_{max}^{KBr}$ (cm$^{-1}$) | NMR: (Hz value represent the coupling constant.) $\delta_{ppm}^{D6-DMSO}$ (internal standard: TMS) | $\delta_{ppm}^{D2O}$ (internal standard: DSS) |
|---|---|---|---|---|
| | (decomposition) −150° C. (coloring) | | (18Hz), 4.65s, 5.22d(5Hz) 1H, 5.34d(5Hz)1H, 7.31–7.77m. | |

We claim:

1. A compound of the formula:

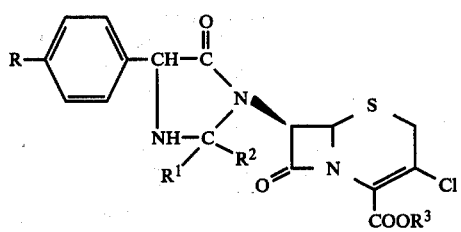

wherein

R is hydrogen or hydroxy,

R$^1$ and R$^2$, independently of each other, are (1) hydrogen, (2) alkyl of 1–4 carbon atoms, (3) phenethyl, (4) benzyl, (5) benzyl substituted by alkyl of 1–3 carbon atoms, alkoxy of 1–3 carbon atoms or halogen, (6) phenyl, (7) phenyl substituted by alkyl of 1–3 carbon atoms, alkoxy of 1–3 carbon atoms or halogen, (8) thienyl or (9) thienyl substituted by alkyl of 1–3 carbon atoms, alkoxy of 1–3 carbon atoms or halogen; or R$^1$ and R$^2$, taken together, represent tetramethylene, pentamethylene, hexamethylene, heptamethylene, azapentamethylene or oxaazapentamethylene, and R$^3$ is hydrogen or a pharmaceutically acceptable carboxylate salt-forming group.

2. A compound claimed in claim 1, wherein R is hydrogen.

3. A compound claimed in claim 1, wherein R$^1$ and/or R$^2$ is hydrogen, methyl, ethyl, propyl, benzyl, chlorobenzyl, methoxybenzyl, phenethyl, phenyl, tolyl, chlorophenyl, methoxyphenyl, thienyl, tetramethylene, pentamethylene, hexamethylene, or ethyleneaminoethylene.

4. A compound claimed in claim 1, wherein R$^3$ is hydrogen.

5. A compound claimed in claim 1, wherein R$^3$ is sodium, potassium or calcium.

6. A compound selected from the group consisting of the following compounds:

(1) 7β-(2-ethyl-5-oxo-4-phenylimidazolidin-1-yl)-3-chloro-3-cephem-4-carboxylic acid;

(2) 7β-(2-ethyl-5-oxo-4-phenylimidazolidin-1-yl)-3-chloro-3-cephem-4-carboxylic acid sodium, potassium or calcium salt;

(3) 7β-(2,2-dimethyl-5-oxo-4-phenylimidazolidin-1-yl)-3-chloro-3-cephem-4-carboxylic acid;

(4) 7β-(2,2-dimethyl-5-oxo-4-phenylimidazolidin-1-yl)-3-chloro-3-cephem-4-carboxylic acid sodium, potassium or calcium salt;

(5) 7β-(2-ethyl-2-methyl-5-oxo-4-phenylimidazolidin-1-yl)-3-chloro-3-cephem-4-carboxylic acid;

(6) 7β-(2-ethyl-2-methyl-5-oxo-4-phenylimidazolidin-1-yl)-3-chloro-3-cephem-4-carboxylic acid sodium, potassium or calcium salt;

(7) 7β-(2-isobutyl-2-methyl-5-oxo-4-phenylimidazolidin-1-yl)-3chloro-3-cephem-4-carboxylic acid;

(8) 7β-(2-isobutyl-2-methyl-5-oxo-4-phenylimidazolidin-1-yl)-3-chloro-3-cephem-4-carboxylic acid sodium, potassium or calcium salt;

(9) 7β-(2,2-tetramethylene-5-oxo-4-phenylimidazolidin-1-yl)-3-chloro-3-cephem-4-carboxylic acid;

(10) 7β-(2,2-tetramethylene-5-oxo-4-phenylimidazolidin-1-yl)-3-chloro-3-cephem-4-carboxylic acid sodium, potassium or calcium salt;

(11) 7β-(2,2-pentamethylene-5-oxo-4-phenylimidazolidin-1-yl)-3-chloro-3-cephem-4-carboxylic acid;

(12) 7β-(2,2-pentamethylene-5-oxo-4-phenylimidazolidin-1-yl)-3-chloro-3-cephem-4-carboxylic acid sodium, potassium or calcium salt;

(13) 7β-(2,2-ethyleneaminoethylene-5-oxo-4-phenylimidazolidin-1-yl)-3-chloro-3-cephem-4-carboxylic acid;

(14) 7β-(2,2-ethyleneaminoethylene-5-oxo-4-phenylimidazolidin-1-yl)-3-chloro-3-cephem-4-carboxylic acid sodium, potassium or calcium salt;

(15) 7β-(2-phenethyl-5-oxo-4-phenylimidazolidin-1-yl)-3-chloro-3-cephem-4-carboxylic acid;

(16) 7β-(2-phenethyl-5-oxo-4-phenylimidazolidin-1-yl)-3-chloro-3-cephem-4-carboxylic acid sodium, potassium or calcium salt;

(17) 7β-(2-phenyl-5-oxo-4-phenylimidazolidin-1-yl)-3-chloro-3-cephem-4-carboxylic acid;

(18) 7β-(2-phenyl-5-oxo-4-phenylimidazolidin-1-yl)-3-chloro-3-cephem-4-carboxylic acid sodium, potassium or calcium salt;

(19) 7β-(2-methyl-2-phenyl-5-oxo-4-phenylimidazolidin-1-yl)-3-chloro-3-cephem-4-carboxylic acid;

(20) 7β-(2-methyl-2-phenyl-5-oxo-4-phenylimidazolidin-1-yl)-3-chloro-3-cephem-4-carboxylic acid sodium, potassium or calcium salt;

(21) 7β-(2-ethyl-2-phenyl-5-oxo-4-phenylimidazolidin-1-yl)-3-chloro-3-cephem-4-carboxylic acid;

(22) 7β-(2-ethyl-2-phenyl-5-oxo-4-phenylimidazolidin-1-yl)-3-chloro-3-cephem-4-carboxylic acid sodium, potassium or calcium salt;

(23) 7β-(2-methoxyphenyl-5-oxo-4-phenylimidazolidin-1-yl)-3-chloro-3-cephem-4-carboxylic acid;

(24) 7β-(2-p-methoxyphenyl-5-oxo-4-phenylimidazolidin-1-yl)-3-chloro-3-cephem-4-carboxylic acid sodium, potassium or calcium salt;

(25) 7β-(2-methyl-2-p-chlorophenyl-5-oxo-4-phenylimidazolidin-1-yl)-3-chloro-3-cephem-4-carboxylic acid;

(26) 7β-(2-methyl-2-p-chlorophenyl-5-oxo-4-phenylimidazolidin-1-yl)-3-chloro-3-cephem-4-carboxylic acid sodium, potassium or calcium salt;

(27) 7β-(2-thienyl-2-methyl-5-oxo-4-phenylimidazolidin-1-yl)-3-chloro-3-cephem-4-carboxylic acid;

(28) 7β-(2-thienyl-2-methyl-5-oxo-4-phenylimidazolidin-1-yl)-3-chloro-3-cephem-4-carboxylic acid sodium, potassium or calcium salt;

(29) 7β-(2,2-dimethyl-5-oxo-4-p-hydroxyphenylimidazolidin-1-yl)-3-chloro-3-cephem-4-carboxylic acid; and

(30) 7β-(2,2-dimethyl-5-oxo-4-p-hydroxyphenylimidazolidin-1-yl)-3-chloro-3-cephem-4-carboxylic acid sodium, potassium or calcium salt.

7. An antibacterial pharmaceutical composition comprising a pharmaceutically effective amount of a compound according to claim 1 and a pharmaceutically acceptable carrier.

8. An antibacterial suppository comprising a pharmaceutically effective amount of a compound according to claim 1 and a pharmaceutically acceptable carrier.

9. A method for treating a human or veterinary infectious disease caused by bacteria sensitive to a compound claimed in claim 1, which comprises administering to the host a pharmaceutically effective amount of the compound by injection or oral, rectal or topical application.

10. A method according to claim 9 wherein administration is by rectal or oral application.

11. An antibacterial capsule containing a pharmaceutically effective amount of a compound according to claim 1 and a pharmaceutically acceptable carrier.

* * * * *